United States Patent [19]

Coates et al.

[11] Patent Number: 4,784,793

[45] Date of Patent: Nov. 15, 1988

[54] TERPENOID DERIVATIVES AND LIQUID CRYSTAL MATERIALS AND DEVICES CONTAINING THEM

[75] Inventors: David Coates, Bishop's Stortford; George W. Gray, Cottingham; David Lacey, Hull; Daniel J. S. Young, Doncaster; Kenneth J. Toyne, Hull; Matthew F. Bone, Bishop's Stortford, all of England

[73] Assignees: The Secretary of State for Defence in Her Britannic Majesty's Government of the United Kingdom of Great Britain and Northern Ireland; STC PLC, both of London, United Kingdom

[21] Appl. No.: 913,671
[22] PCT Filed: Jan. 24, 1986
[86] PCT No.: PCT/GB86/00046
§ 371 Date: Nov. 26, 1986
§ 102(e) Date: Nov. 26, 1986
[87] PCT Pub. No.: WO86/04328
PCT Pub. Date: Jul. 31, 1986

[30] Foreign Application Priority Data
Jan. 26, 1985 [GB] United Kingdom ............... 8501999

[51] Int. Cl.$^4$ .................. G02F 1/13; C07C 69/76; C07C 119/10; C07D 239/26; C09K 19/34; C09K 19/12; C09K 19/20; C09K 19/52
[52] U.S. Cl. ..................... 252/299.62; 252/299.01; 252/299.5; 252/299.63; 252/299.64; 252/299.65; 252/299.66; 252/299.67; 252/299.68; 350/350 F; 350/350 S; 560/55; 560/59; 560/73; 560/102; 560/106; 560/107; 560/108; 560/109; 560/113
[58] Field of Search ............ 350/350 S, 350 R; 252/299.63, 299.5, 299.61, 299.62, 299.64, 299.65, 299.66, 299.67, 299.68, 299.01; 560/55, 59, 73, 102, 106, 107, 108, 109, 113

[56] References Cited
U.S. PATENT DOCUMENTS

| 4,514,045 | 4/1985 | Huffman et al. ............... 252/299.1 |
| 4,576,732 | 3/1986 | Isolai et al. ............... 252/299.65 |
| 4,596,667 | 6/1986 | Inukai et al. ............... 252/299.66 |
| 4,613,209 | 9/1986 | Goodby et al. ............... 252/299.65 |
| 4,614,609 | 9/1986 | Inoue et al. ............... 252/299.66 |
| 4,615,586 | 10/1986 | Geary et al. ............... 252/299.01 |

FOREIGN PATENT DOCUMENTS

| 56-92836 | 7/1981 | Japan ............... 252/299.63 |
| 57-40581 | 3/1982 | Japan ............... 252/299.63 |
| 8602937 | 5/1986 | World Int. Prop. O. ....... 252/299.66 |
| 8602938 | 5/1986 | World Int. Prop. O. ....... 252/299.66 |

OTHER PUBLICATIONS

Malthete, J. et al., Mol. Cryst. Liq. Cryst., vol. 54, pp. 45–50 (1979).
Chilaya, G. S., et al., Advances in Liquid Crystal Research & Applications, Data, L. Ed., Pergamon Press, Oxford, pp. 1185–1189 (1980).
Elashvili, Z. M., et al., J. De Physique, vol. 40, No. 4, Coll. C3, pp. C3-22-24 (1979).
Melone, S., et al., Molicryst. Liq. Cryst., vol. 98, pp. 399–409 (1983).
Goodby, J. W., et al., JACS, vol. 108, No. 16, pp. 4736–4742 (1986).
Gerber, P. R., Liquid Crystals & Ordered Fluids, vol. 4, Griffin, A. C., et al., Plenum Press, N.Y., pp. 999–1010 (1984).
C.A., vol. 93, 26558h (1980).
C.A., Vol. 77, 158095j (1977).

Primary Examiner—Teddy S. Gron
Attorney, Agent, or Firm—Stevens, Davis, Miller & Mosher

[57] ABSTRACT

Novel derivatives of cyclic and acyclic terpenoid alcohols, having general formula (I) X—(CO)$_n$—O—T$_1$, where n=0 or 1, T$_1$ is a terpenoid group and X is a combination of cyclic groups, e.g. phenyl, cyclohexyl and pyrimidyl, X preferably contains up to three cyclic groups. Preferred derivatives are esters of cyclic terpenoid alcohols, e.g. menthol, borneol and isopineocampheol, e.g. formula (II) (−)-menthol. Ferroelectric smectic liquid crystal mixtures and devices containing these derivatives as chiral dopants in a tilted smectic host are also described. The properties of various other derivatives of terpenoid alcohols of formula (I) are also described, e.g. those of neomenthol, isolongifolol, fenchol, carveol, myrthenol, nopol, citronellol, perilla alcohol and dihydrocitronellol.

16 Claims, 2 Drawing Sheets

TERPENOID DERIVATIVES AND LIQUID CRYSTAL MATERIALS AND DEVICES CONTAINING THEM

This invention relates to liquid crystal compounds and liquid crystal mixtures which exhibit ferroelectric properties.

The first work on ferroelectric switching liquid crystal display devices by N A Clark and S T Lagerwall reported in Applied Physics Letter Vol. 36 No. 11 pp 899–901 (June, 1980) (Reference 1) used DOBAMBC or HOBACPC as the ferroelectric liquid crystal. These materials are, for most applications, far from ideal because they are relatively unstable chemically and sensitive to light, their spontaneous polarisation coefficients are relatively small, and their tilted smectic phases are at inconveniently high temperatures and exist over inconveniently high temperatures and exist over inconveniently small temperature ranges.

This invention is concerned with the provision of ferroelectric liquid crystal mixtures having larger coefficients of spontaneous polarisation ($P_s$) and improved temperature range of tilted smectic phases.

We believe that the relatively small values of $P_s$ exhibited by DOBAMBC and HOBACPC result at least in part from the relatively free rotation in these molecules of the chiral group relative to the remainder of the molecule. It is suggested that a molecule with the same or similar polarity on its chiral group should, in the absence of conflicting factors, exhibit enhanced spontaneous polarisation if the structure of the molecule is modified to increase the steric hindrance to hinder the rotation of the chiral group. However, it is usually the case that the means by which steric hindrance can be achieved militates against the formation of liquid crystal phases, particularly those with a relatively wide temperature range.

The present invention is therefore directed to ferroelectric liquid crystal mixtures having two major constituents neither of which on its own necessarily exhibits any spontaneous polarisation. One of these two constituents, which does not on its own necessarily exhibit any tilted smectic phase, and hence does not on its own necessarily have to exhibit any spontaneous polarisation, is or contains at least one compound which is optically active (chiral) and exhibits a high degree of steric hindrance of the chiral group of its molecule relative to the remainder of the molecule. This first constitutent, which may be a single compound or a mixture is generally described in ferroelectric liquid crystal chemistry as a "dopant".

The second constituent is provided by a material that is compatible with the first constituent and exhibits a tilted smectic phase, C, I, F, J, K, G, H or X (abbreviated herein to "$S_C$" etc), over an acceptably wide temperature range. This second material does not necessarily contain any chiral centre in its molecular structure, and hence it likewise does not on its own necessarily have to exhibit any spontaneous polarisation. This second constituent, which may also be a single compound or a mixture, is generally described as a "host" in ferroelectric liquid crystal chemistry. The smetic C phase is generally preferred as this is the most fluid.

These two constituents act co-operatively in the mixture, with the host serving to provide the requisite tilted smectic phase of a ferroelectric mixture, while the dopant provides the requisite chirality of the resulting chiral tilted smectic phase of the mixture, and preferably also inducing a high Ps in the mixture. Chiral smectic liquid crystal phases are identified herein by S*, e.g. $S_C^*$.

According to a first aspect of the present invention there is provided an ester which is a derivative of a terpenoid alcohol and which has the formula (1):

$$X-(CO)_n-O-T_1 \qquad \text{Formula (1)}$$

wherein $T_1$ is a terpenoid group, n is 0 or 1, wherein X is a group having the formula:

$$R_1-(A)_a-B_1-(A_2)_b-B_2-(A_3)_c-B_3-(A_4)_d-L-$$

wherein L is a 1,4-linked phenyl group optionally carrying one or more lateral substituents, or a 2,6- or 1,4-linked naphthalene group optionally laterally substituted in one or more positions, or a 1,4-linked phenyl group having one or two =CH— groups replaced by nitrogen, particularly a 2,5-linked 1,3-pyrimidine;

wherein each of $A_1$, $A_2$, $A_3$ and $A_4$ independently represents a 1,4-linked phenyl group optionally carrying one or more lateral substituents, or a 2,6- or 1,4-naphthalene group optionally laterally substituted in one or more positions, or a 1,4-phenyl group having one or two =CH— groups replaced by nitrogen, particularly 2,5-linked 1,3-pyrimidine, or a 1,4-linked cyclohexane ring, preferably in the trans configuration, optionally carrying one or more lateral substituents or having one or two methylene groups replaced by oxygen or sulphur, particularly 2,5-linked 1,3-dioxan, or 1,4-linked bicyclo (2,2,2) octane;

wherein a is 1, and each of b, c and d independently is 0 or 1;

wherein each of $B_1$, $B_2$ and $B_3$ independently represents a single covalent bond or a linking group selected from —CO.O—, —O.OC—, —CH=N—, —N=CH—.

—N=N—, —CH$_2$O—, —O.CH$_2$, —CH$_2$.CHD—, or —CHD. CH$_2$—, where D is methyl, cyano, halogeno or —CF$_3$;

and wherein $R_1$ contains not more than 18 carbon atoms and represents an alkyl, alkoxy, fluoroalkyl, fluoroalkoxy, alkanoyl, alkanoyloxy, alkyl carbonyl oxy, alkoxycarbonyl, halogeno, cyano, or $T_2$—O.OC— group, where $T_2$ has the same designation as $T_1$ without $T_1$ and $T_2$ necessarily being identical.

Preferably $R_1$ contains between 6 and 12 carbon atoms and is alkyl, alkoxy or alkanoyl.

If any or all of L, $A_1$, $A_2$, $A_3$, $A_4$ are 1,4-linked phenyl groups containing lateral substituents, such substituents are preferably located at positions tending to hinder intramolecular rotation in the molecule and to increase the dipole moment.

Similarly, in $A_1$ to $A_4$ substituents are preferably arranged partly with the object of fixing the orientation of each of the cyclic groups $A_1$ to $A_4$ with respect to its neighbours and partly with the object of adding to the total lateral dipole moment of the molecule. Preferred substituents are methyl, methoxy, trifluoromethyl, cyano, halogeno, acetyl groups.

Where any of $A_1$ to $A_4$ represents a 1,4-linked cyclohexane group a lateral substituent is preferred in the 1 and/or 4 positions.

Preferably not more than one of b, c, and d is 1.

Samples of preferred groups $X-(CO)_nO-$ where Y is halogen or the preferred substituents as identified above, are listed in Table 1 below.

also rings of five, four or three carbons. Terpenoids are often obtained from biosynthetic sources, and in the course of biosynthesis terpenes are sometimes produced which either lack part of an iosprene unit or has an extra part of one. Sometimes migration of methyls occurs so that the final biosynthetic product may no longer have a skeleton strictly composed of isoprene units. These

TABLE 1

$T_1$, and $T_2$ is present, may be selected from the group consisting of residues of monocyclic monoterpenes, bicyclic monoterpenes, tricyclic sesquiterpenes and acyclic terpenes.

Terpenoids are derivatives of the analogous terpenes, which are isoprene oligomers. The term "terpenoid" as used herein includes not only the saturated or unsaturated isoprene oligomers themselves, but also their oxygenated derivatives and partial or complete reduction products. The majority of terpenoids contain cyclic polyisoprene chains, usually six-membered rings, but materials are nevertheless considered to be members of the terpenoid family.

Many terpenoids exist in an optically active form, ie containing one or more asymmetric carbon atoms, as a single enantiomer, indicated herein either by a designation of its optical handedness, ie D or L, or by a designation of its absolute configuration, ie R or S, or by a symbol (+) or (−) indicating the sense of optical rotation, in which case the compound of Formula I may be prepared in an optically active form.

Alternatively many terpenoids exist as racemic systems or have structures which cannot be optically active, in which case the compounds of the invention may be prepared in a racemic or non-optically active form.

The —(CO)$_n$O-group may be linked to the terpenoid in any position, but compounds wherein rotation of the terpenoid group relative to the X-group is hindered or prevented by the presence of adjacent substituent groups are preferred, eg the compound (2)

Compounds of Formula 1 which are esters, ie n=1 may easily be prepared by esterification of the appropriate carboxylic acid X—COOH with an appropriate terpenoid alcohol T$_1$—OH or T$_2$—OH with the —OH group of the alcohol in a suitable position.

Examples of optically active monocyclic monoterpenoid alcohols include menthol, neomenthol, isomenthol, neoisomenthol, carveol, dihydrocarveol, terpinen —4-ol, -terpineol, and limonen —10-ol; examples of optically active bicyclic monoterpenoid alcohols include borneol, isoborneol, fenchol, verbenol, camphenilol, myrtenol, nopol and perilla alcohol, while examples of chiral tricyclic sesquiterpenoid alcohols include cedrol and isolongifolol. Examples of acyclic terpenoid alchols include citronellol and dihydrocitronellol. Many of these alcohols may be obtained as S or R enantiomers.

The esterification process may be carried out by conventional reactions. The carboxylic acids may in some cases be commercially available or may in other cases be prepared by hydrolysis of the corresponding nitrile, or oxidation of an acetyl group. If it is desired to prepare an optically active ester, then the products should be checked of each step to ensure that racemisation has not occurred.

A suitable route is Route A below:
Route A (i) Hydrolysis
(ii) Thionyl Chloride, reflux.
(iii) Pyridine, solvent.

If the group X contains groups which are likely to react with thionyl chloride, eg those which contain the —CH=N— group (ie Schiffs bases), then Route B below may be used, which comprises a novel combination of well known steps: Route B (i) Thionyl chloride, refux.
(ii) Pyridine, solvent, T$_1$OH.
(iii) Iron dust/acetic acid in ethanol solvent.
(iv)

in ethanol solvent, trace of acetic acid. Where R may be an alkyl group and T$_1$OH is a terpenoid alcohol. The application of these routes to other groups X in Formula 1 will be well known to those skilled in the art.

According to a second aspect of the invention there is provided a ferroelectric smectic liquid crystal material, being a mixture of at least two compounds, at least one of which is a derivative of a terpenoid alcohol.

The derivative is preferably an ester of the terpenoid alcohol.

The derivative may be optionally active, in which case it may be capable of functioning as a chiral dopant to induce a chiral tilted smectic liquid crystal phase in a mixture with a smectic host, preferably also inducing a high Ps. Although it is likely to be beneficial if the derivative exhibits a tilted smectic phase, this is not essential for its functioning as a dopant.

Alternatively the derivative may comprise, or be a component of a smectic host, particularly if the derivative is in a racemic form or is a derivative of a non-chiral terpenoid. The derivative may itself show a tilted smectic liquid crystal phase.

In such a racemic or non-optically active form the terpenoid derivative will not show a Ps, but may still be useful as, or in a host, particularly if the derivative has an $S_C$ liquid crystal phase. In a compound of Formula I, there is usually more likelihood of the compound showing an $S_C$ phase if all the cyclic groups in X are aromatic.

Among their other advantages, derivatives of terpenoids are particularly useful in that being often available from biological sourcse (eg various plant oils) they may be cheap relative to wholly synthetic compounds. In addition, by virtue of their biosynthetic origin they are often available as exclusively one optical enantiomer, and thus require no tedious resolution, which again makes them cheap relative to synthetic optically pure compounds.

The terpenoid derivative is preferably a compound of Formula 1, as the structures defined by Formula 1 are most likely to be liquid crystals.

The possibility of obtaining terpenoid derivatives as single optical enantiomers makes them particularly suitable as chiral dopants in ferroelectric smectic host-dopant liquid crystal mixtures. For use as dopants in such mixtures, for the reasons discussed herein, esters of terpenoid alcohols with an acid are preferred, eg compounds of Formula I wherein n is 1, rather than the ethers wherein n is 0, and the bulky cyclic terpenoid alcohols are preferred to the acyclic terpenoid alcohols.

Another advantage of the use of optically active terpenoid derivatives in liquid crystal materials according to this aspect of the invention is that they may be used in a mixture containing a chiral dopant (which may itself be a terpenoid derivative) which induces a helical twist in the smectic phase which is of opposite sense to that induces by the terpenoid derivative, eg by means of the chiral dopant and the terpenoid derivative having opposite optical handedness, ie one D and the other L. They may thus be used to "unwind" the helical smectic lattice and increase the pitch length. This effect is particularly useful when the sense of polarisation induced by the terpenoid derivative is the same as that induced by the chiral dopant, so as to be additive, in which case a smectic phase of long pitch, preferably infinite pitch, but of high Ps may be obtained.

For example a ferroelectric smectic liquid crystal material may contain a derivative of lactic acid as a chiral dopant, being the R-stereoisomer and inducing a (—) sense of Ps, and may also contain a terpenoid derivative being the S-stereoisomer, yet also inducing a (—) sense of Ps.

Examples of chiral dopants which may be used in this way with a terpenoid derivative include, among others, the following:

(i) Derivatives of lactic acid, eg as described in PCT application PCT/GB No. 85/00512, such as the compounds below;

(the S-(—) enantiomers may also be used).

(ii) Derivatives of amino acids, eg as described in UK patent applications Nos. 8520714 an 8524879, such as the compounds;

(iii) Derivatives of secondary alcohols, eg as described in UK patent application No. 852071, such as the 2-octanol esters;

or various esters of 2-methylbutyl, such as;

where $R_x$ is $C_6$–$C_{12}$ n-alkyl or n-alkoxy.

It is believed that esters of terpenoid alcohols are good dopants in ferroelectric smectic liquid crystal mixtures because of the steric hindrance to rotation of the bulky chiral terpenoid group. It has been found however that in esters of terpenoid alcohols, eg compounds of Formula (1), two conflicting effects occur. A small side group on the terpenoid ring, eg derivatives of isopinocampheol (3):

(3)

promotes the appearance of $S_c$ phases, whilst large side groups on the terpenoid ring eg derivatives of menthol (4):

(4)

induce a high $P_s$. On balance isopineocampheol derivatives are preferred as chiral dopants.

Furthermore in the case of terpenoid esters, eg compounds of Formula 1, a chiral terpenoid group is held relatively close to the remainder of the molecule by the ester link, which has a beneficial effect in inducing a high $P_s$ as discussed below.

Measured values of the spontaneous polarisations of two ferroelectric smectics having the same core demonstrate the effect of the movement of the chiral group away from the core. Thus compound (5), the optically active (S-isomer) chiral ester marketed by BDH Chemicals under the designation CE8, (5)

exhibits in the $S_C*$ phase a spontaneous polarisation, ($P_s$) of 2.0 nCcm$^{-2}$, whereas for compound (6)

(6)

the measured value under corresponding conditions is 0.14 nCcm$^{-2}$. From these comparative figures it is seen that the magnitude of $P_s$ in the $S_C*$ phase decreases dramatically as the chiral centre is moved further away from the core. We attribute this to the increased freedom of rotation of the chiral centre in compound (6) as compared with that of the chiral centre in compound (5). Confirmation of this appears to be provided by corresponding measurements made on the compound (7)

(7)

where an increase in steric hindrance of the chiral centre has been provided by attaching the 2-methyl butyl group in close proximity to the carbonyl group of an ester. For compound (7) the measured value of $P_s$ in the $S_C*$ phase is 3-4 nCcm$^{-2}$. In such esters the core does not appear to play such a vital role in determining $P_s$ value, as is indicated by the fact that the corresponding Ps value for compound (8), DOBAMBC, (8)

in the $S_C*$ phase is also 3-4 nCcm$^{-2}$.

The use of a more polar group on the chiral carbon has the effect of increasing the spontaneous polarisation. Thus the comparative figure for compound (9), HOBACPC, (9)

in the $S_C*$ phase is 18 nCcm$^{-2}$. Other esters of optically active 2-chloropropanol also show a similar value of spontaneous polarisation. Thus compound (10)

(10)

exhibts an extrapolated spontaneous polarisation of 20 nCcm$^{-2}$. For the purpose of this measurement the compound was dissolved in a S*C phase host, in this particular instance the racemic ester marketed by BDH Chemicals under the designation racemic CE8. (The "Extrapolated Ps" was calculated by extrapolating the measured value to 100% of the compound).

From the attainment of relatively high Ps values attributed to a reduction of the free rotation of the chiral centre with respect to the main core of the molecule, it follows that, if rotation is significantly reduced, then there is no longer any intrinsic need to provide a chiral centre which has a strong dipole moment. The dipole can advantageously be incorporated into the core of the molecule. This has several advantages including the ease of synthesis, the option to use more than one polar group, and generally a greater chemical stability.

One particular way of reducing the free rotation of the chiral group is to locate the chiral centre as close as possible to the main core of the molecule, for instance by having it directly bonded to the carboxyl group of the aromatic acid part of an ester. A specific example is the ester (11)

(11)

The $S_C*$ phase of this compound is very monotropic and hence its $P_s$ is difficult to measure directly. However, by making measurements upon solutions of the compound in a suitable host, in this instance racemic CE8, an extrapolated Ps value of 20.8 nCcm$^{-2}$ was obtained at 10° C. below the $S_A$-$S_C*$ transition.

Reduction of free rotation can also be achieved by the use of lactic acid as the chiral group. This results in an increased dipole moment compared with that of compound (11). This increases the Ps of the mixtures incorporating these compounds. Although these compounds do not usually possess a tilted phase, and therefore cannot be ferroelectric, they do impart a high degree of ferroelectricity to non-chiral tilted phases which in themselves are not ferroelectric. (It can be advantageous if the host tilted phase does possess a residual spontaneous dipole moment, as long as it is of the same sign as the added lactate ester).

An example of such compounds is (12)

when 18.6 weight % of (12) is mixed with racemic CE8 the Ps values inciated in Table 3 were found.

TABLE 3

| °C. below the $S_A$-$S_C$* transition | Ps nCcm$^{-2}$ | Extrapolated Ps nCcm$^{-2}$ |
|---|---|---|
| 5° | 10 | 54 |
| 10° | 13.5 | 73 |

This use of lactic acid based esters is disclosed in Patent Appln. Nos. 8428653 and 8500765 and PCT/GB No. 85/00512.

In the present invention the use of a chiral group based on lactic acid is replaced by the use of the terpenoid based chiral group. A feature of this substitution is the resulting enlargement of the chiral group by means of a terpenoid ring system.

With the terpenoid derivatives of the invention rotation of the terpenoid group with respect to the remainder of the molecule is further prevented by the ester carbonyl acting either directly upon on adjacent aromatic ring in the acid part of the molecule, eg a compound of Formula 1, or upon one or more substituents attached to that ring. An example of such a compound is the (−)-menthol ester (13)

compound (13) does not exhibit a smectic phase, but when mixed as a 10.8 weight % solution with racemic CE8 the $P_s$ values listed in Table 4 were found.

TABLE 4

| °C. below the $S_A$-$S_C$* transition | Ps nCcm$^{-2}$ | Extrapolated Ps nCcm$^{-2}$ |
|---|---|---|
| 5° | 5.7 | 53 |
| 10° | 8.4 | 78 |

The extrapolated values of $P_s$ (extrapolated to 100%) for compound (13), the menthol based material, (53 and 78 nCcm$^{-2}$) are thus seen to be higher than the corresponding figures for compound (12), the lactate based material (53 and 72 nCcm$^{-2}$).

It is noteworthy that the menthol based material shows the higher spontaneous polarisation notwithstanding the fact that the only polar groups in menthol are methyl groups, whereas lactic acid possesses a much more strongly polar group, the carbonyl group.

It is also believed that when significant steric hindrance is present, any transverse polarisation associated with polar substitutents at locations of the molecule other than at the chiral group should also make a contribution to the attainment of a high value of spontaneous polarisation. In this context it is important to note that it is generally easier to incorporate highly polar substituents at sites elsewhere than on the chiral group, and that in man instances it is possible to provide more than one such substituent, and to locate them such that their effect is additive.

Liquid crystal materials according to this aspect of the invention may comprise a terpenoid derivative in a mixture with a wide range of host materials. Some considerations should however be taken into account in selecting a host.

One of the particular advantages of the use of the two distinct constituents (host and dopant) of the ferroelectric smectic mixture is that it eases the problem of obtaining a material that will exhibit a high $P_s$ over a relatively wide temperature range. The molecular form of the dopant can be structured with the primary aim of providing a large transverse polarisation notwithstanding the fact that this is liable to militate against a wide temperature range of tilted smectic phase (if indeed such a phase is ever present in the dopant). Correspondingly the host material can be formulated with the primary aim of providing the mixture with a wide temperature range of tilted smectic phase to cover the required service temperature range.

The main core of the first constituent should be compatible with the smectic phase molecular lattice so that it is prevented from tumbling, or excessive motion, in relation to the host. To this end it has in many cases been found that hosts and dopants having the same or similar molecular core are compatible, eg the compound racemic PG495 would be expected to be compatible with the terpenoid derivative (14):

It should also be appreciated that high solubility is also a desirable characteristic for the dopant insofar as it affords the possibility of a greater proportion of this constituent in the mixture and hence, in general, a greater value for the spontaneous polarisation. In general the host material exhibiting a tilted smectic phase, will not normally be a single chemical compound, but will be a eutectic mixture of several compounds. Likewise, though the dopant may be a single chemical compound, there is likely to be advantage in many circumstances in employing a mixture of different compounds.

This provides a method of determining the usefulness of a compound of the invention, for example measurement of the Ps of the compound. In practice the Ps of the solution of the compound in a host material, eg a racemic smectic host which shows a Ps of 0 without any of the compound is measured, and an 'extrapolated Ps' for the pure compound of the invention is derived from this by known methods. It has been observed that in many cases a high extrapolated Ps is found in a com- pound of Formula I which shows a high optical rotation angle.

A wide range of suitable host materials is known, with which compounds of the invention may be mixed. Some examples are:

(a) The compounds and compositions disclosed in European patent application No. 0110299A2.
(b) The compounds and compositions disclosed in Mol. Cryst. Liq. Cryst, 37, 157 (1976), eg esters having a central core of the structure:

(c) The known compounds of formula:

(or mixtures of them, which may be a racemic mixture) where $R_C$ and $R_D$ independently represent n-alkyl or n-alkoxy at least one of which is a chiral group. For example where $R_C=n-C_8H_{17}$ and $R_D=(+)-2$ methylbutyl, the compound is commercially available from BDH Chemicals Ltd, Broom Road, Poole, Dorset, UK.

(d) The compounds and compositions disclosed in UK patent application No. 8501509, for example those of formulae Ia to Ih on P2 of that application such as:

(e) The known compounds, or mixtures thereof, having a formula where one of $R_A$ and $R_B$ represents $C_{5-12}$n-alkoxy and the other represents $C_{7-12}$n-alkyl or n-alkoxy. These compounds are nonchiral.

(f) The known compound racemic PG495

(racemic)

(g) The known compounds where R and R' are independantly $C_6$–$C_{10}$ n-alkyl.
(h) The known compounds or mixtures of them.

Both (f) and (h) above are available from BDH Chemicals Ltd.

Other suitable smectic host materials which may be mixed with compounds of Formula I will be apparent to those skilled in the art. A mixture which contains one or more compounds of the invention, and exhibits a chiral smectic phase may have added to it one or more additives to engineer other preferred properties for a particular device such as viscosity, dielectric anistropy, birefringence, pitch, elastic constants, melting point, clearing point etc. Additives showing a weak longitudinal dipole moment (eg compounds containing alkyl and/or alkoxy terminal groups) are preferred. Preferably they show a lateral dipole moment (eg by containing a lateral halogen, $CF_3$ or CN substituent).

In the field of smectic liquid crystal chemistry relatively little is known about the structural requirements for miscibility and it is therefore somewhat difficult to predict which compounds will form stable mixtures with smectic phases. It may thus be necessary to carry out some relatively straightforward experiments to determine whether a particular combination of compounds such as a host, or additives as discussed above will form a stable mixture. Such experiments may in many cases comprise no more than melting a combination of compounds together (if they are not liquid at room temperature) and observing the appearance or otherwise of smectic phases by known methods such as optical microscopy.

Most research to date in this relatively new field has been concentrated on finding good working combinations of host and dopant and it is expected that future work will be directed towards refining and improving those combinations with additives.

There are some signs that compounds which have the same or a closely related molecular core or combination of cyclic groups and linking groups in their structure will be misable, for example the compound PG 495 is miscible with its analogue having the 2-methylbutyl ester group replaced by a terpenoid ester. That this principle is not absolutely rigid is demonstrated by the wide range of compounds which are miscible with PG 495 and RCE 8 in tables 7 to 12.

Some possible examples of additives are given in Table 4 below, but it must be understood that this is only a general guide and experiments should be carried out in all cases to investigate suitability.

Examples of low melting and/or low viscosity additives are the compounds shown in Table 4.

TABLE 4 where each R is independently alkyl or alkoxy, eg $C_{1-18}$ n-alkyl or n-alkoxy, and each $R_A$ is independently alkyl, eg $C_{1-18}$ n-alkyl.

An example of a mixture according to this aspect of the invention is the following:

| | | |
|---|---|---|
| (a) | One or more of compounds (a) to (h) above (host). | up to 99 wt. % preferably up to 95 wt. % |
| (b) | One or more of the compounds of Table above. | up to 30 wt. % |
| (c) | A compound of the invention, optionally plus one or more other compounds of the invention or one or more other. chiral dopants, eg of the types (i). (ii), (iii), or (iv) above in a ratio which gives a suitable pitch length and Ps. | 5 to 50 wt. % |

The amount of each compound made up to 100% with one or more compounds of the invention contained in the mixtures of the invention depends on the properties required of the mixture, including the Ps value and the pitch of the molecular configuration in the chiral smectic phase. When the compound of the invention induces an increased Ps in the host, the Ps value induced generally increases with the amount of the compound which is present in the host.

Some examples of the preparation of compounds of Formula (1), and of their use in liquid crystal mixtures and in devices utilising them will now be described with reference to the accompanying drawings in which.

In these examples the following abbreviations symbols and terminology are used:
C = Solid crystal.
I = Isotropic liquid
Ch = Cholesteric liquid cyrstal phase $[\alpha]_D^T$ = optical rotation angle at T°C using Sodium D line.

All temperatures are in °C.

$S_C - S_A = T$ = smectic C to smectic A transition at T°C, other liquid crystal transitions denoted analagously.

D,L = optical handedness Dexto, Laevo.
$P_s$ = spontaneous polarisation in $nCcm^{-2}$, extrapolated to 100% from the value in a solution of known concentration.

Signs of $P_s$, ie (+), (−) according to the convention of Lagerwall and Dahl, Mol-Cryst. Liq-Cryst 114 151-187 (1984).

In this description represents a trans-cyclohexane ring. For clarity, cyclohexane rings in terpenoid structures are represented by

EXAMPLE 1

Preparation of (−) menthyl 4-n-decyloxybiphenyl-4'-carboxylate (compound (13)) by Route A 4-n-Decyloxybiphenyl-4'-carboxylic acid (2 g; 0.0056 m), which had been prepared by hydrolysis of 4-cyano-4'-n-decyloxybiphenyl (supplied by BDH, Poole, Dorset), was heated under reflux for 3 hours with thionyl chloride (39 ml). The thionyl chloride was then removed on a rotary evaporator; residual thionyl chloride was next evaporated off by azeotropic distillation using dry benzene.

The acid chloride was dissolved in dry pyridine (30 ml) and cooled in an ice bath. (−)-Menthol (0.94 g; 0.006 m) $[\alpha]_D^{16} = -44°$ was dissolved in the minimum volume of dry pyridine and added to the acid chloride solution over a period of 15 minutes. The reagents were stirred for 1 hour in the ice bath, then overnight at room temperature, and finally for 2 hours at 60° C. After cooling, the mixture was poured into dilute hydrochloric (100 ml), and the product extracted into dichloromethane (100 ml). The dichloromethane layer was washed with dilute hydrochloric acid solution (100 ml) a further five times, and then with water (100 ml) and finally with a dilute solution of sodium bicarbonate (100 ml). After drying the dichloromethane solution with magnesium sulphate, it was rotary evaporated to leave a low melting point solid. This was purified by column chromatography on silica gel (70–130 mesh) using 1 part dichloromethane to 2 parts light petroleum (b.p. 40°–60° C.) as eluent. The isolated solid was crystallised from I.M.S. to constant melting point and single spot purity by thin layer chromoatography. The melting point of the final product was 26° C., and evidence that it was indeed an ester was provided by the presence of an infra-red absorption peak at 1710 cm$^{-1}$ corresponding to the C=O stretching vibration frequency.

The $P_s$ values of this compound in solution in racemic CE8 have been given in Table 4 above, together with the extrapolated $P_s$.

The optical handedness was L, and the $P_s$ sign (−). The compound showed a C−I transition at 26° C.

EXAMPLE 2

The above preparation method was repeated using 4-n-octyloxybiphenyl-4'-carboxylic acid and (−) menthol. The melting point of the product was 57°–58° C. From measurements upon a solution of 3–14 weight % of this product in racemic CE8 extrapolated values of $P_s$ for this material of 52 and 71.6 nCm$^{-2}$ were calculated respectively for temperatures of 5° and 10° C. below the $S_A$-$S_C$* transition.

The optical handedness was L and the $P_s$ sign was (−).

The properties of other terpenoid derivatives which were made by a method identical to that of Example 1 using the appropriate acid and the terpenoid alcohol indicated are listed below:

EXAMPLE 3

D—(−)-Borneol $P_s$ in racemic CE8 10° C. below $S_C$*−$S_A$=28

$C-I=92°$ C.

optical handedness L
$P_s$ sign (+)

EXAMPLE 4

(+)-Neomenthol

Not sufficiently soluble in racemic CE8 to obtain meaningful $P_s$ value.

$C-I=62°$ C.

optical handedness D
$P_s$ sign (−)

EXAMPLE 5

(−)-Isolongifolol

Too insoluble to measure a $P_s$ value.
Mpt.=81° C.
optical handedness L
$P_s$ sign (+)

EXAMPLE 6

(+)-Fenchol $C-I=71°$ C.

optical handedness D
$P_s$ sign (−)

EXAMPLE 7

(−)-Carveol

Obtained as oil, mixture of isomers

EXAMPLE 8

(+)-Menthol

Ps in racemic CE8 at 10° C. below $S_C$*−$S_A$=72

$C-I=62°$

Optical handedness D, Ps sign (+)

EXAMPLE 9

(−)-Menthol $C-I=125.7°$ C.

optical handedness L
$P_s$ sign (−)

EXAMPLE 10

(−)-Isopinocampheol $P_s$ in racemic CE8 at 10° C. below $S_C*-S_A=28$ $C-S_C=172$ $(S_C-S_A)=138)$ $S_A-Ch=178$ $Ch-I=186.2$ optical handedness D
$P_s$ sign (−)

Figure 1:
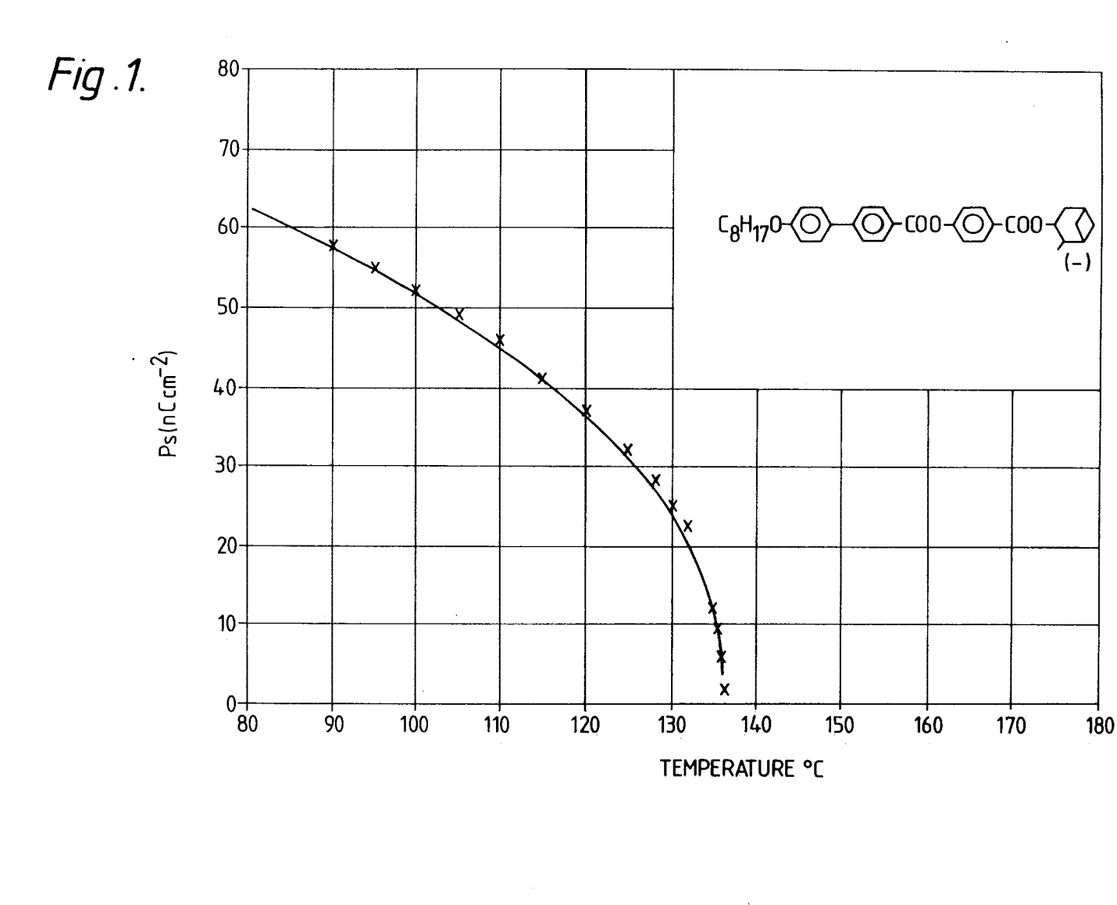
FIG. 1 shows a plot of $P_s$ against temperature of a compound of the invention.

A plot of $P_s$ against temperature °C. of this compound is shown in FIG. 1. From this plot the relationship $P_s(nCcm^{-2})=\alpha(T-Tc)^\beta$ Where T = temperature of measurement, Tc = temperature of transition to liquid crystal phase at temperature above $S_C$ was obtained where:
$\alpha=10.421$
$\beta=0.445$
Transition Temp = 136.51

EXAMPLE 11

(−)-Isopineocampheol $C-S_A=124°$ C.

$(S_A-S_C=97.5°$ C.)

$(S_C-S?=82°$ C.)

$S_A-Ch=145°$ C.

$Ch-I=156°$ C.

EXAMPLE 12

(−)-Menthol $C-I=91.5°$ C.

EXAMPLE 13

(−)-Menthol $C-I=108°$ C.

EXAMPLE 14

L-(−)-Menthol $C-I=41.3-43.1$

EXAMPLE 15

(−)-Myrtenol colourless oil,
boiling point 250° C./6×10⁻³ mbar.

EXAMPLE 16

(−)-Nopol $C-I=41$

EXAMPLE 17

L-(—)-Borneol

C—I=100

EXAMPLE 18

L-(—)-Menthol

C—I=87.8-88.7

EXAMPLE 19

(+)-Neomenthol melting point 38.7
clearing point 51.0

EXAMPLE 20

This compound was prepared using route B above.

(—)-Menthol

EXAMPLE 20
(contd.)

C—I=84

Ps in racemic CE8 10° C. below $S_C$—$S_A$=68
optical handedness L
Ps sign (—)

EXAMPLE 21

S—(—)-Citronellol

IR (KBr) shows C=O stretch at 1732 cm$^{-1}$ (no liquid crystal data available)

EXAMPLE 22

S—Dihydrocitronellol melting point 45.5°–46°
clearing point 55.5°

EXAMPLE 23

S—Dihydrocitronellol boiling point 250° C./2×10$^{-3}$ mbar.

The following Examples, 24–27 are ethers of terpenoid alcohols, and were prepared by a method analogous to that used in Example 24, which is of general applicability.

Tetrabutylammoniumhydrogensulphate (7.8 g; 23 mmol) and nopolmethanesulphonate (56.7 g; 232 mmol) were adder to a stirred solution of 5-n-nonyl-2-(4-hydroxyphenyl)-pyrimidine (69.2 g; 232 mmol) in toluene (300 ml). After addition of 67 ml of aqueous sodium hydroxide (32%) at 60° C. to the suspension ant stirring overnight the reaction mixture was worked up as normal. The isolated solid was recrystallised from acetone.

EXAMPLE 24

(—)-Nopol

C—I=42°

EXAMPLE 25

(—)-Perilla alcohol

C—I=100°

EXAMPLE 26

S—(—)-Citronellol colourless oil
boiling point 250° C./4×10$^{-3}$ mbar

EXAMPLE 27

S—Dihydrocitronellol colourless oil
boiling point 250°/4×10$^{-3}$ mbar

The following two Examples, 28 and 29 are examples of liquid crystal mixtures containing terpenoid derivatives.

EXAMPLE 28

The following is an example of a mixture of terpenoid esters which induce opposite twist senses in a chiral smectic phase, but which induce additive Ps senses:

C$_8$H$_{17}$O—⟨⟩—⟨⟩—COO—⟨⟩—COO—⟨⟩   98 wt %

(isopinocampheol, D— configuration)

C$_8$H$_{17}$O—⟨⟩—⟨⟩—COO—⟨⟩—COO—⟨⟩   2 wt %

((—)-menthol, L— configuration)

This mixture has an S$_C$ phase of infinite pitch and shows a Ps of ca. 30 nCcm$^{-2}$ at a temperature 10° C. below S$_C$—S$_A$.

EXAMPLE 29

| | |
|---|---|
| 2-p-hexyloxyphenyl-5-heptylpyrimidine | 3 wt % |
| 2-p-heptyloxyphenyl-5-heptylpyrimidine | 3 wt % |
| 2-p-octyloxyphenyl-5-heptylpyrimidine | 3 wt % |
| 2-p-nonyloxyphenyl-5-heptylpyrimidine | 3 wt. % |
| 2-p-hexyloxyphenyl-5-nonylpyrimidine | 7 wt. % |
| 2-p-nonyloxyphenyl-5-nonylpyrimidine | 27 wt. % |
| r-1-cyano-cis-4-(4'-octyloxybiphenyl-4-yl)-1-butylcyclohexane | 26 wt. % |
| r-1-cyano-cis-4-(4'-heptylbiphenyl-4-yl)-1-hexylcyclohexane | 13 wt. % |
| r-1-cyano-cis-4-(trans-4-pentylcyclohexyl)-1-(trans-4-pentylcyclohexyl)-cyclohexane | 5 wt. % |
| (-)-menthyl p-trans-4-heptylcyclohexylbenzoate | 10 wt. % | shows:
Solid crystal—S$_C$=0° C., S$_C$—S$_A$=65, S$_A$—Ch=85 and a Ps value of 3.9 nCcm$^{-2}$ at 25° C.

This mixture therefore shows a useful room temperature ferroelectric smectic phase.

Figure 2:
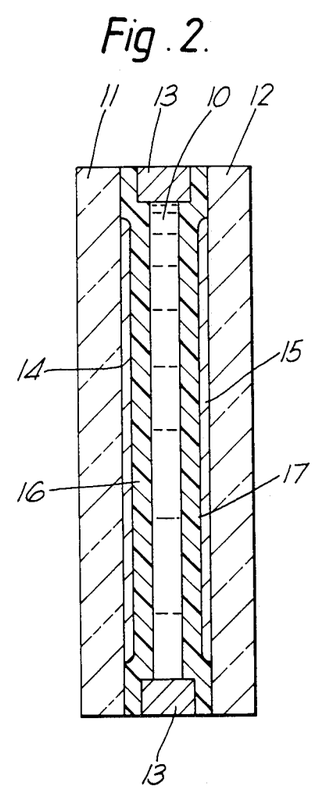
FIG. 2 shows a sectional view of a liquid crystal device using a mixture of the invention.

Referring now to FIG. 2 hermetically sealed envelope for a liquid crystal layer if formed by securing together two glass sheets 11 and 12 with a perimeter seal 13. The inward facing surfaces of the two sheets carry transparent electrode layers 14 and 15 of indium tin oxide, and each of these electrode layers is covered within the display area defined by the perimeter seal with a polymer layer, such as polyimide (16,17), provided for molecular alignment purposes. Both polyimide layers are rubbed in a single direction so that when a liquid crystal is brought into contact with them they will tend to promote planar alignment of the liquid crystal molecules in the direction of the rubbing. The cell is assembled with the rubbing directions aligned parallel with each other. The thickness of the liquid crystal layer contained within the resulting envelope is determined by the thickness of the perimeter seal, and control over the precision of this may be provided by a small number of short lengths of glass fibre (not shown) of uniform diameter distributed through the material of the perimeter seal or within the envelope itself.

Conveniently the cell is filled by applying a vacuum to an aperture (not shown) through one of the glass sheets in one corner of the area enclosed by the perimeter seal so as to cause the liquid crystal medium to enter the cell by way of another aperture (not shown) located in the diagonally opposite corner. (Subsequent to the filling operation the two apertures are sealed). The filling operation is carried out with the filling material heated into its isotropic phase as to reduce its viscosity to a suitably low value. It will be noted that the basic construction of the cell is similar to that of for instance a conventional twisted nematic, except of course for the parallel alignment of the rubbing directions.

Typically the thickness of the perimeter seal 13, and hence of the liquid crystal layer, is about 10 microns, but thinner or thicker layer thicknesses may be required to suit particular applications depending for instance upon whether or not bistability of operation is required and upon whether the layer is to be operated in the S$_c$* phase or in one of the more ordered phases such as S$_I$* or S$_F$*.

The liquid crystal filling is a two-constituent ferroelectric mixture as hereinbefore defined. The first constituent may for instance, be one of the materials specifically described with reference to the examples or a mixture of such materials. In the foregoing description specific two-constituent mixtures have employed racemic CE8 as the second (host) constituent. While CE8 is a suitable material for illustrating the properties of first constituent materials, it is not particularly well suited to actual display applications because of the relatively narrow temperature range of its tilted smectic phases, and moreover because this range is significantly above room temperature. Accordingly for the second constituent of a non-experimental device it is generally preferred not to employ CE8 as the sole component of the second constituent but to employ a mixture such as:

| Compound | wt. % |
|---|---|
| C$_8$H$_{17}$O—⟨⟩—CO.O—⟨⟩—OC$_5$H$_{11}$ | 31.6 |

-continued

| Compound | wt. % |
|---|---|
|  | 38.7 |
| $C_7H_{15}$—⟨O⟩—CO.O—⟨O⟩—$OC_8H_{17}$ | |
| $C_8H_{17}O$—⟨O⟩—CO.O—⟨O⟩—$OC_6H_{13}$ | 29.7 |

This mixture showed the liquid crystal phase transitions:

$C-S_C = 20°$ C., $S_C-N = 46°$ C.

The mixture of Example 29, with its room temperature $S_C$ phase could also be used in the cell described above. Such cells may be used in display applications, optical switching applications, and optical information processing applications etc.

What is claimed is:

1. An ester of a terpenoid alcohol which has a formula:

(I)

$R_1$—⟨O⟩—(COO)$_a$—⟨O⟩—(COO)$_b$—COO—$T_1$ wherein $R_1$ is $C_1$–$C_{18}$ alkyl or alkoxy, each of a and b is 0 or 1 provided that (a+b) is 0 or 1, and $T_1$ represents the residue of a terpenoid alcohol selected from the group consisting of borneol, fenchol, isopinocampheol, nopol, perilla alcohol and dihydrocitronellol.

2. An ester according to claim 1, which is an ester of isopinocampheol in which $T_1$ has a structure:

3. An ester according to claim 2, having a formula:

$R_1$—⟨O⟩—⟨O⟩—COO—⟨O⟩—COO—⟨bicyclic⟩.

4. An ester according to claim 1, having a formula $R_1$—⟨O⟩—⟨O⟩—COO—$T_1$ wherein $T_1$ is the residue of a terpenoid alcohol selected from the group consisting of borneol, fenchol and dihydrocitronellol.

5. An ester according to claim 1, having a formula $R_1$—⟨O⟩—COO—⟨O⟩—COO—$T_1$ wherein $T_1$ is the residue of a terpenoid alcohol selected from the group consisting of borneol and nopol.

6. An ester according to any one of claims 1 to 5 wherein $R_1$ is selected from the group consisting of $C_8$ to $C_{10}$ n-alkyl or n-alkoxy.

7. A ferroelectric smectic liquid crystal material which is a mixture of compounds, at least one of which is an ester of a terpenoid alcohol which has a formula:

$R_1$—⟨O⟩—(C—COO)$_a$—⟨O⟩—(COO)$_b$—COO—$T_1$ wherein $R_1$ is $C_1$–$C_{18}$ alkyl or alkoxy, each of a and b is 0 or 1 provided that (a+b) is 0 or 1, and $T_1$ represents the residue of a terpenoid alcohol selected from the group consisting of borneol, fenchol, isopinocampheol, nopol, perilla alcohol and dihydrocitronellol.

8. A material as claimed in claim 7, wherein the ester is optically active.

9. A material as claimed in claim 8, wherein the ester is an ester of (−)-isopinocampheol.

10. A material as claimed in claim 9, wherein the ester has a formula

$R_1$—⟨O⟩—⟨O⟩—COO—⟨O⟩—COO—⟨bicyclic⟩.

11. A material as claimed in claim 10, wherein $R_1$ is $C_8$–$C_{10}$ n-alkyl or n-alkoxy.

12. A material as claimed in claim 8, wherein the material also contains an additional optically active compound which induces a helical twist in the smectic phase which is of the opposite sense to that induced by the said ester.

13. A material as claimed in claim 12, wherein the said ester is an ester of (−)-isopinocampheol.

14. A material as claimed in claim 13, wherein the said ester has a formula $R_1$—⟨O⟩—⟨O⟩—COO—⟨O⟩—COO—⟨bicyclic⟩.

15. A material as claimed in claim 14, wherein $R_1$ is $C_8$–$C_{10}$ n-alkyl or n-alkoxy.

16. A liquid crystal electro-optical display device which incorporates as its liquid crystal material a material as claimed in any one of claims 7 to 15.

* * * * *